(12) United States Patent
Harttig et al.

(10) Patent No.: US 8,404,478 B2
(45) Date of Patent: Mar. 26, 2013

(54) DIAGNOSTIC TEST TAPE FOR LIQUID SAMPLES

(75) Inventors: Herbert Harttig, Neustadt (DE); Josef Roeper, Neuhofen (DE); Otto Fuerst, Viernheim (DE); Thomas Jaeck, Heddesheim (DE); Ralf Dagenbach, Schwetzingen (DE); Juergen Braun, Ehningen (DE); Ronald Moench, Ilvesheim (DE); Hans List, Hesseneck-Kallbach (DE); Beate Koschorreck, Schriesheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/205,886

(22) Filed: Aug. 9, 2011

(65) Prior Publication Data

US 2012/0045825 A1 Feb. 23, 2012

Related U.S. Application Data

(63) Continuation of application No. PCT/EP2010/051811, filed on Feb. 12, 2010.

(30) Foreign Application Priority Data

Feb. 13, 2009 (EP) .................................. 09152837

(51) Int. Cl.
*C12M 1/34* (2006.01)
*C12M 3/00* (2006.01)
*G01N 21/62* (2006.01)
*G01N 33/558* (2006.01)

(52) U.S. Cl. ............... 435/287.1; 435/287.2; 435/287.3; 435/287.9; 436/170; 436/514; 422/56

(58) Field of Classification Search ............... 435/287.2, 435/287.3, 287.9; 436/170, 514; 422/56
See application file for complete search history.

(56) References Cited

U.S. PATENT DOCUMENTS

| 4,587,099 | A | 5/1986 | Rothe et al. | |
|---|---|---|---|---|
| 4,758,337 | A | * 7/1988 | Kohn et al. | ..................... 210/94 |
| 5,411,858 | A | 5/1995 | McGeehan et al. | |
| 5,846,837 | A | 12/1998 | Thym et al. | |
| 6,537,496 | B1 | 3/2003 | Knappe et al. | |
| 7,479,253 | B2 | 1/2009 | Knappe et al. | |
| 7,820,451 | B2 | 10/2010 | Brauner | |

(Continued)

FOREIGN PATENT DOCUMENTS

| CA | 1001537 | 12/1976 |
|---|---|---|
| DE | 2 118 455 | 9/1972 |

(Continued)

OTHER PUBLICATIONS

International Preliminary Report on Patentability, International Application No. PCT/EP2010/051811, 11 pages.

*Primary Examiner* — Nathan Bowers
*Assistant Examiner* — Lydia Edwards
(74) *Attorney, Agent, or Firm* — Krieg DeVault LLP

(57) ABSTRACT

A diagnostic test tape for liquid samples is provided comprising a flexible transport tape and a plurality of test fields applied to the transport tape that are distributed in the longitudinal direction of the tape, where said test fields comprise a detection layer and a spreading net spanning the detection layer for a planar uptake of liquid sample, wherein the spreading net is formed from a lattice-like fabric comprising fabric threads that cross at right angles. In order to prevent the fabric from arching up under tape tension it is proposed that the fabric is oriented obliquely to the transport tape such that all fabric threads run obliquely to the longitudinal direction of the tape.

20 Claims, 4 Drawing Sheets

U.S. PATENT DOCUMENTS

| | | |
|---|---|---|
| 7,857,924 B2 | 12/2010 | Roeper et al. |
| 7,961,303 B2 | 6/2011 | Sacherer |
| 2006/0002816 A1* | 1/2006 | Zimmer et al. ............... 422/56 |
| 2007/0258860 A1* | 11/2007 | Tanaka ...................... 422/68.1 |
| 2009/0241783 A1* | 10/2009 | Kitagawa et al. ............ 99/323 |

FOREIGN PATENT DOCUMENTS

| | | |
|---|---|---|
| DE | 196 29 657 A1 | 1/1998 |
| EP | 0 064 710 | 11/1982 |
| EP | 0 209 032 | 1/1987 |
| EP | 0 821 233 A2 | 1/1998 |
| EP | 0 995 993 A2 | 4/2000 |
| EP | 1 522 343 A1 | 4/2005 |
| EP | 1 593 434 A2 | 11/2005 |
| EP | 1 834 696 A1 | 9/2007 |
| EP | 1 878 379 A1 | 1/2008 |
| WO | WO2008035443 * | 3/2008 |

* cited by examiner

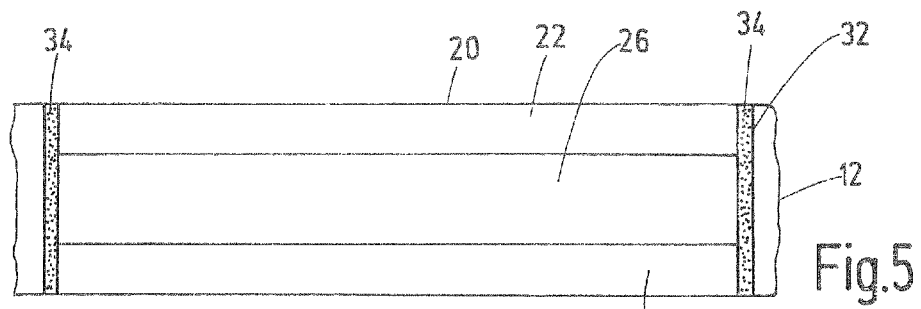
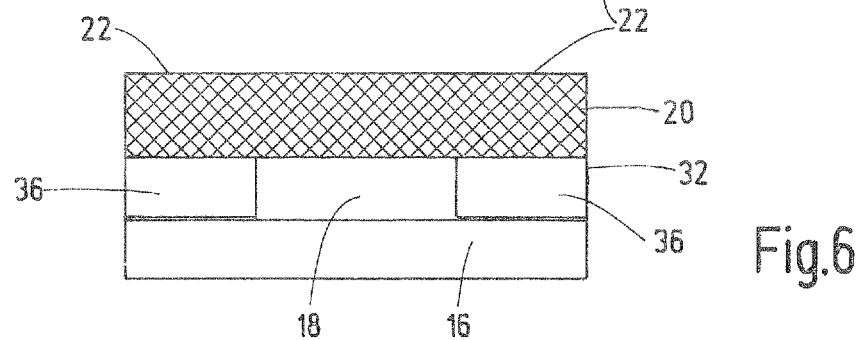
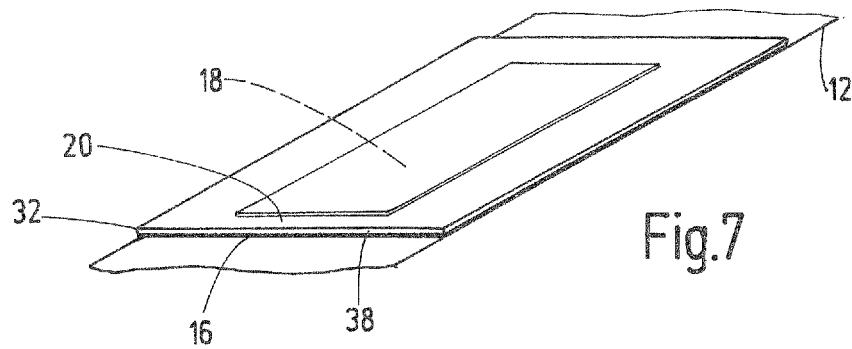
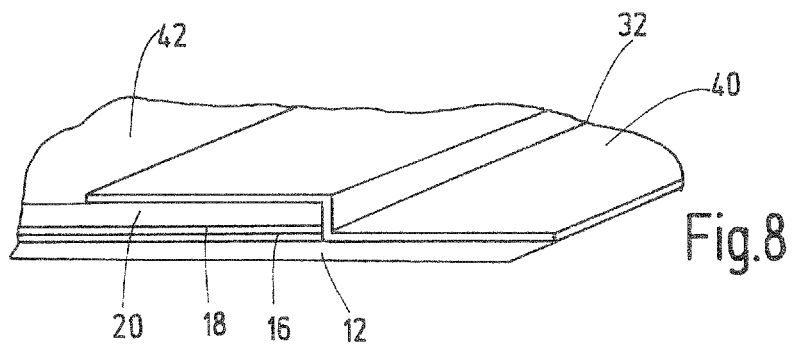
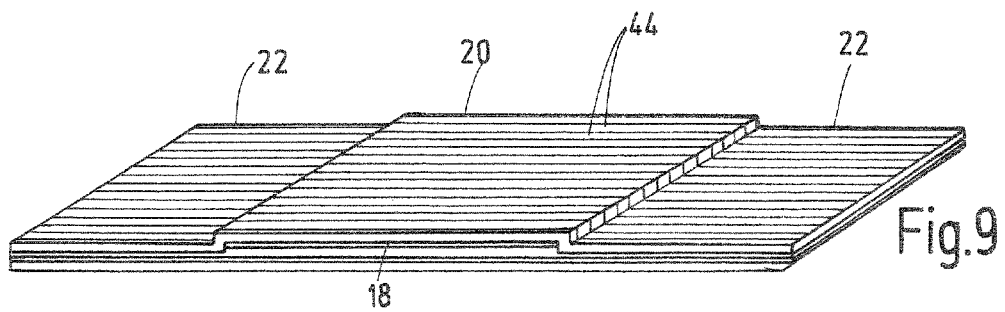

DIAGNOSTIC TEST TAPE FOR LIQUID SAMPLES

CROSS-REFERENCE TO RELATED APPLICATIONS

This application is a continuation of International Application No. PCT/EP2010/051811 filed Feb. 12, 2010, which claims priority to EP Application No. 09152837.2 filed Feb. 13, 2009. Each of the referenced applications is incorporated herein by reference in its entirety.

FIELD OF THE INVENTION

The invention concerns a diagnostic test tape for liquid samples, in particular for body fluids, comprising a flexible transport tape that is wound onto or can be wound onto a spool and a plurality of test fields applied to the transport tape that are distributed in the longitudinal direction of the tape, said test fields comprising a detection layer and a spreading net spanning the detection layer for a planar uptake of liquid sample.

BACKGROUND

Diagnostic test tape systems are designed especially for blood sugar tests in order to further improve the user friendliness compared to the test strip systems that are on the market. Thus, in order to simplify the handling, a large number of test units or test fields can be stored on a rollable transport tape in a compact manner and they can also be disposed of again after use by the tape transport. A simple assembly procedure for a test tape of this type is disclosed in EP 1 593 434. Thus, roll-to-roll processing with a high manufacturing speed is possible. In this connection the fabric used as a spreading aid to improve the distribution of the liquid sample is only held by an adhesive layer in the area of its protruding longitudinal edges for process-related reasons. However, if the fabric becomes detached from the detection layer, this can result in a non-uniform wetting with the blood sample which hinders a correct analysis. Furthermore, the spreading fabric may also not become detached from the test field until after the test field has been wetted with blood. The blood then flows into the area of fabric that is still resting on it and forms air bubbles in the separated area of fabric which have a negative effect on the measurement analysis.

SUMMARY

On this basis the invention further improves the known products in the prior art and provides a robust tape assembly which is also optimized with regard to mass production for a reliable sample processing.

A first aspect of the invention is based on the idea of harmonizing the stretching properties of the carrier tape and of the spreading fabric. Accordingly it is proposed according to the invention that the fabric is oriented obliquely to the transport tape such that all fabric threads run obliquely to the longitudinal direction of the tape. This arrangement prevents only one thread system from being subjected to a tensile load. Rather a load is placed on all fabric threads depending on their inclination when a tensile force acts on the carrier tape thus resulting in a certain ratio of transverse contraction and linear expansion also for the fabric. This can substantially reduce differences in the transverse shrinkage of the fabric and of the remaining test tape assembly so that an unwanted lifting or bulging of the spreading aid is prevented. Existing mesh materials can be adapted with little effort to the properties of the carrier tape and of the test field in order to substantially exclude the risk of an uneven wetting of the test field with test liquid and subsequent falsification of the analytical result.

The orientation of the fabric is advantageously defined such that under a given tensile load the difference in the transverse contraction of the transport tape and of the fabric is minimized.

Depending on the material properties it is advantageous when the fabric has an oblique orientation at a compensation angle in a range between 5° and 40°, preferably 20° to 25° where the compensation angle is defined by the smallest angle between the longitudinal direction of the tape and the fabric threads.

Taking into consideration the conditions for use it is advantageous when the transport tape consists of a foil material having a Poisson number of 0.3 to 0.5, preferably of about 0.4.

Also with regard to a simplified manufacture it is advantageous when the fabric in plain weave is formed from warp yarns and weft yarns and when the warp yarns run nearer to the longitudinal direction of the tape than the weft yarns.

Another improvement provides that the optionally hydrophilically coated fabric threads consist of a monofilament thread material in particular of a polyester such as PET.

The inclination allows a simple test field assembly to be achieved without problems where the spreading net is broader than the detection layer and is glued in the area of its protruding side edges to a carrier strip carrying the detection layer which is applied to the transport tape.

Another aspect of the invention is that the spreading net is additionally secured against lifting from the detection layer by a protection against lifting in addition to or alternatively to a lateral glueing. In this connection it can also be ensured that the distance between the spreading net and detection layer under the conditions of use is no more than 40 micrometers, preferably less than 20 micrometers to substantially exclude the risk of an uneven wetting even if caused by capillary forces.

An advantageous variant provides that the front ends of the rectangular spreading net each have a material bond running at right angles to the longitudinal direction of the tape and preferably a laser-welded seam as a protection against lifting. The laser-welded seam can in this case be formed in an advantageous manner for manufacturing by a laser cut while cutting the test field to length from rolls.

According to a further advantageous embodiment the spreading net is wider than the detection layer and is supported in the area of its protruding side edges by strips of adhesive tape as a protection against lifting on the carrier strip. In this connection the strips of adhesive tape as spacers and the detection layer can have essentially the same thickness so that the spreading net rests flat thereon.

In another advantageous embodiment the spreading net is attached circumferentially to the carrier strip by an adhesive frame as a protection against lifting which runs all around the detection layer. For this purpose the adhesive frame can advantageously be formed by laser welding and/or by spots of hot glue.

Another advantageous embodiment can be that the width of the spreading net at right angles to the longitudinal direction of the tape is identical to or less than that of the detection layer and that the longitudinal edges of the said spreading net are attached by an overlapping adhesive tape as a protection against lifting while a central application window is kept free. In this case it is also advantageous when the area forming the application window is punched out of the adhesive tape.

Another advantageous embodiment of the protection against lifting provides that the spreading net consists of a lattice-like fabric having a bend-resistant thread system that can be deformed in a stepped manner in the direction transverse to the tape. For this purpose it is advantageous when the fabric is provided with weft yarns made of metal.

A protection against lifting can also be realized in that the carrier strip consists of a robust foil material the shear strength of which is more than 0.05 N/mm² and which has a peel strength of more than 1 N/mm.

The invention also concerns a tape cassette comprising a diagnostic test ape according to the invention, which test tape is guided over a deflection point preferably with a tape tensile force of more than 1 N for sample application.

BRIEF DESCRIPTION OF THE DRAWINGS

The invention is further elucidated in the following on the basis of the embodiment examples shown schematically in the drawings.

FIGS. 5 to 9 each shows a section of test tape with various embodiments of a protection against lifting for the spreading fabric.

DETAILED DESCRIPTION

Figure 1:
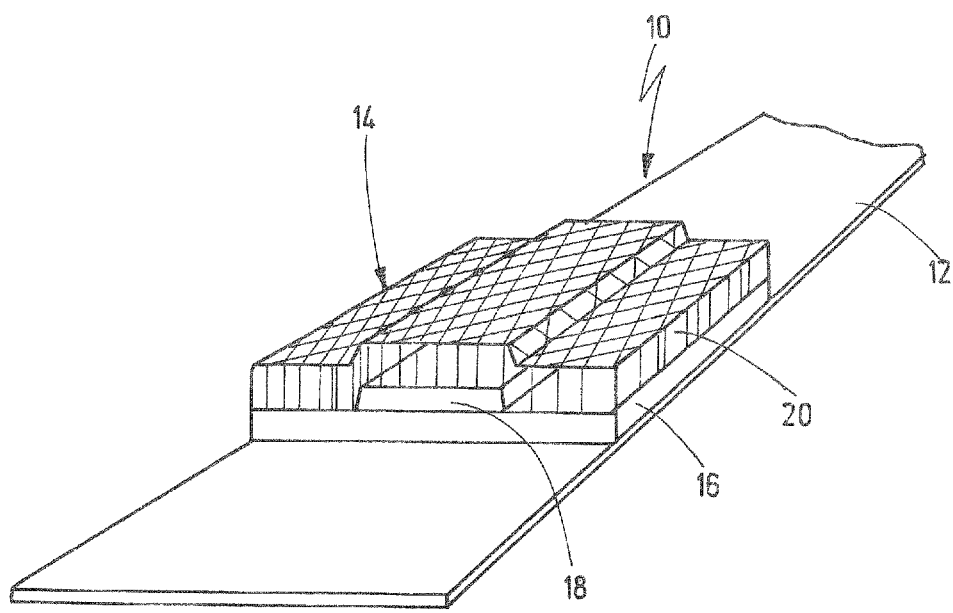
FIG. 1 shows a test tape with an analytical test field in a cut-off perspective diagram.

The diagnostic test tape 10 shown in the drawing for carrying out blood sugar tests comprises a windable flexible transport tape 12 and a plurality of test elements or test fields 14 that are stored thereon for successive single use and are spaced apart from one another in the longitudinal direction of the tape, the test fields as label-like flat structures having a rectangular contour and comprising a carrier strip 16 glued onto the transport, tape 12, a detection layer 18 applied thereon and a spreading net 20 spanning the detection layer 18 on the upper side facing away from the carrier strip for a planar distribution of a sample liquid (blood sample) applied from above to the spreading net. The detection layer 18 reacts as a dry chemistry film, in particular on an enzyme basis, to an analyte (glucose) by a colour change so that a photometric detection can take place through the transparent foil composite 12, 16.

Figure 2:
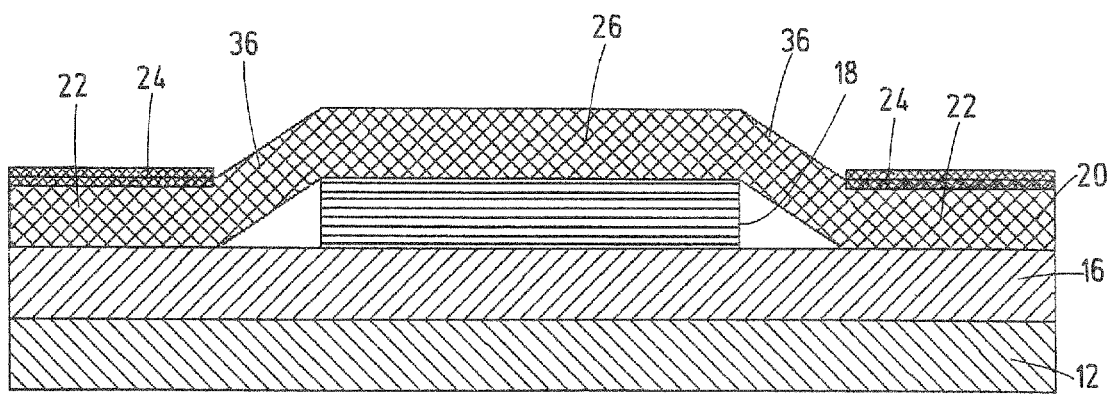
FIG. 2 shows a cross-section through the test tape according to FIG. 1 in the area of the test field.

As shown in FIGS. 1 and 2 the strip-shaped spreading net in the form of a fabric 20 is wider than the detection layer 18. The protruding side edges 22 of the fabric 20 are glued to the upper side of the carrier strip 16 which in turn is glued onto the transport tape 12 as a double-sided piece of adhesive tape. The free outer side of the side edges 22 of the fabric 20 are provided with a hydrophobic coating 24 so that the liquid distribution or spreading can occur specifically in the non-glued central area 26 of the fabric 20 over the detection layer 18.

The test fields 14 can be successively brought into use by advancing the transport tape 12 to an application site. The flexible tape structure is subjected to a longitudinal stretching and transverse contraction due to the tensile force that is exerted in this process which could lead to a lifting or arching upwards of the central area 26 of the fabric over the detection layer 18. This effect is due to the fact that the length but not the width of a fabric oriented in the tape longitudinal direction is changed by tape tensile forces whereas the width of the carrier ape 12 is reduced by transverse contraction.

Figure 3:
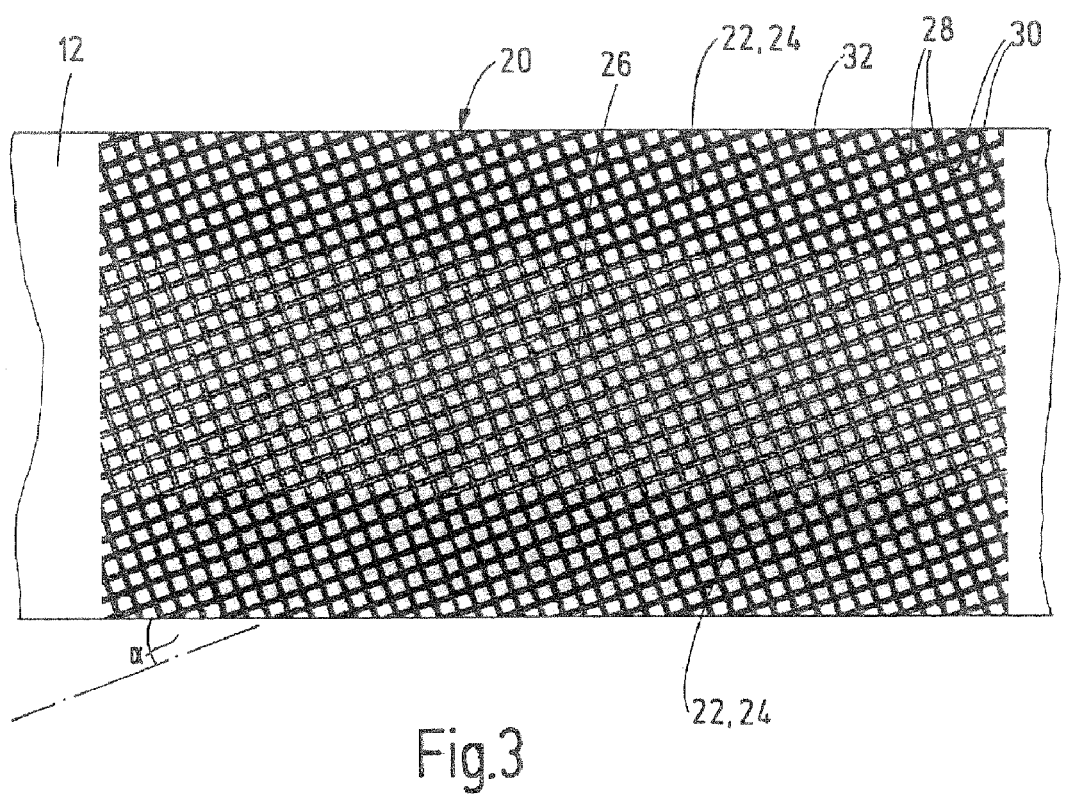
FIG. 3 shows a top-view of the test tape according to FIG. 1 in the area of an obliquely oriented spreading fabric covering the test field.

In order to avoid this lifting effect which is disadvantageous for a uniform blood distribution, the fabric 20 is oriented obliquely to the transport tape 12 as shown in FIG. 3. The fabric 20 has fabric threads 28, 30 which cross at right angles and which all run obliquely to the longitudinal tape direction or to the tape edges 32.

The fabric 20 in plain-weave is advantageously formed from warp yarns 28 and weft yarns 30 which consist of PET in the form of monofilaments. For processing rolls of material it is advantageous when the long warp yarns 28 run nearer to the longitudinal tape direction than the short weft yarns 30.

The orientation of the fabric 20 can be specified by a compensation angle α which is defined by the smallest angle between a tape edge 30 and the fabric threads (i.e. in FIG. 3 by the warp yarns 28).

Figure 4:
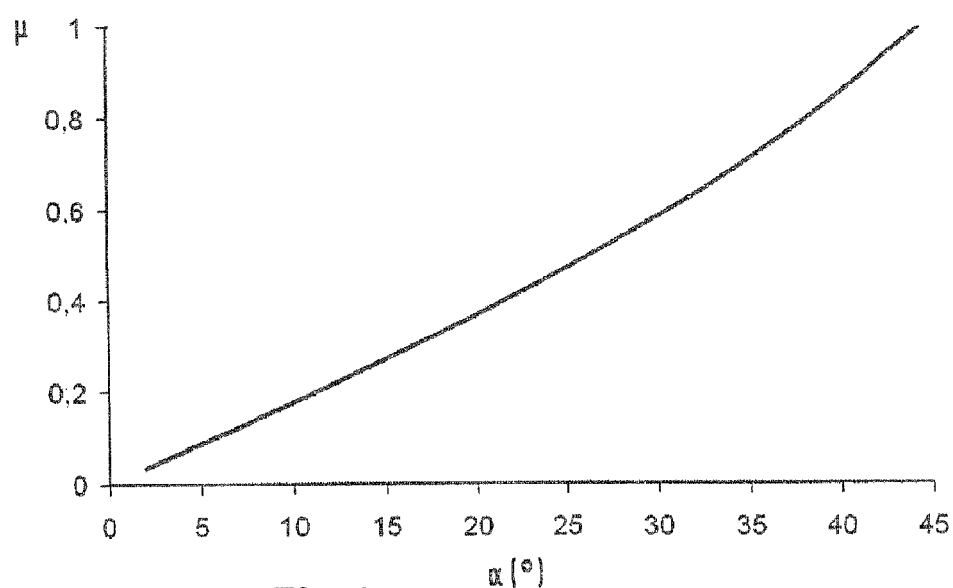
FIG. 4 shows a diagram of the Poisson number as a function of the orientation angle of the spreading fabric according to FIG. 3.

FIG. 4 shows the dependency of the Poisson number μ on the compensation angle α of the fabric 20. In general the Poisson number gives the change in the transverse dimension d as a ratio to the longitudinal stretching ΔL of a body of length L according to the following relationship:

$$\mu = \frac{\Delta d / d}{\Delta L / L}$$

The oblique alignment of the fabric 20 is determined such that under a predetermined tensile load the difference in the transverse contraction of the transport tape 12 and of the fabric 20 is minimized. At a given Poisson number of the carrier tape 12 of about 0.4, the compensation angle should thus be in a range between 20° and 25°.

In the embodiment examples shown in FIGS. 5 to 9 the same or similar parts have the same reference numerals as in the above description. Here the spreading net 20 is secured against bulging or lifting from the detection layer 18 by a protection against lifting 32 instead of by an inclined orientation. In the various embodiment examples this protection against lifting 32 is provided in addition to or complementary to the lateral glueing of the side edges 22 of the spreading net 20 to the carrier strips 16. The embodiment of the spreading net 20 in this case is not only limited to fabric but can also encompass other flat structures as liquid distributors such as a porous membrane. In any case the protection against lifting 32 is designed such that the distance between the central area 26 of the spreading net 20 and the detection layer 18 is no more than 40 μm and preferably less than 20 μm under the operating conditions of the test tape.

In the embodiment shown in FIG. 5 the rectangular spreading net 20 is secured on its front ends pointing in the longitudinal tape direction by a transverse continuous laser-welded seam 34. This attachment can occur by melting the net material when the test fields 14 are cut by a laser as described in more detail in the following.

A further improvement in the robustness of the test tape 10 is due to the fact that the bevel 36 that can be seen in FIG. 2 is avoided in the cross-sectional profile of the spreading net 20.

This can be achieved according to FIG. 6 in that the spreading net 20 is wider than the detection layer 18 and is laterally supported on the carrier strip 16 in the area of its protruding side edges 22 by strips of adhesive tape 36 acting as a protection against lifting 32. In this case the strips of adhesive tape 36 should have essentially the same thickness as the detection layer 18 so that the spreading net 20 lies flat.

FIG. 7 shows an embodiment example in which the front ends of the spreading net 20 also protrude beyond the detection layer 18 and the underside of the spreading net is attached all around to the carrier strip 16 by a circumferential adhesive frame 38 as a protection against lifting 32. This can take place by laser welding or a combination of adhesive foils and laser welding. One manufacturing method is also to use an adhesive foil with spots of hot adhesive as an intermediate carrier in the tape manufacturing process in order to transfer adhesive spots to the short and long sides of the adhesive frame 38 in a precise manner.

In the embodiment example shown in FIG. 8 the spreading net 20 has at most the same width as the detection layer 18 so that the net cannot bulge in the relaxed state. All components are then attached by means of lateral adhesive tapes 40 as a protection against lifting 32. Thus, the adhesive tape 40 overlaps the longitudinal edges of the layered structure 16, 18, 20 while keeping a central application window 42 free for the application of the liquid sample. It is also possible that the area forming the application window 42 is punched out of a transverse continuous piece of adhesive tape 40.

FIG. 9 illustrates an embodiment example in which the spreading net 20 is provided with a bend-resistant thread system 44 running at right angles to the tape direction as a protection against lifting 32. The transverse threads are in this case designed such that they can be pressed against the edge of the detection layer 18 substantially without an air gap. This can advantageously be achieved by using a fabric 20 with weft yarns made of metal.

Another possibility of improving the robustness is to select a suitable foil material for the carrier strip 16. Such a material should have a shear strength in the range of 40 N/625 mm$^2$ (according to DIN EN 1943) whereas the peel strength should be about 25 N/25 mm$^2$ (according to DIN EN 1939). Such a foil material can for example be obtained under the trade name Duplocoll VP20242.

Figure 10:
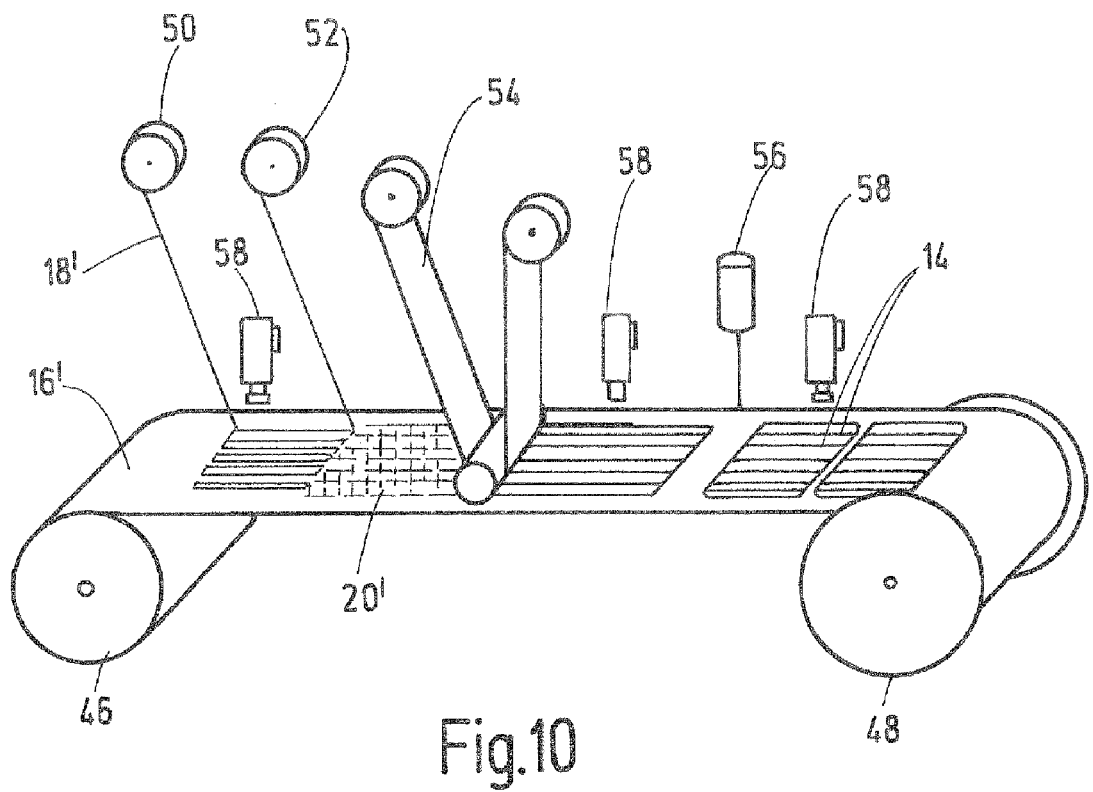
FIG. 10 shows a schematic of the test field manufacture using roll material.

In order to enable a high manufacturing rate and flexibility in the production of the test tape 10, a roll-pull-roll process is provided. FIG. 10 shows a preliminary stage for the multi-lane manufacture of the test fields 14. In this process a double-sided adhesive tape is transported by a production line between two rolls 46, 48. Several parallel detection films 18' are applied thereto from the spools 50. The arrangement is overlaid with spreading fabric 20' which is pulled from further spools 52. The layer assembly is subsequently fastened by means of a thermotransfer foil 54. Then laser cuts running at right angles which separate the parallel test fields 14 from one another at their ends are introduced with a laser 56. If the parameters are suitably selected, the laser 56 can not only cut the test fields 14 to length but also glue the edge areas to one another to form the welded seam 34 (FIG. 5). The entire process is monitored by a camera system 58 so that waste is substantially avoided. Test fields 14 pre-fabricated in this manner can be transferred and glued onto a transport tape 12 in a label-like manner over a dispensing edge in the process of which the test tapes 10 manufactured in a multi-lane process are then cut lengthways.

Figure 11:
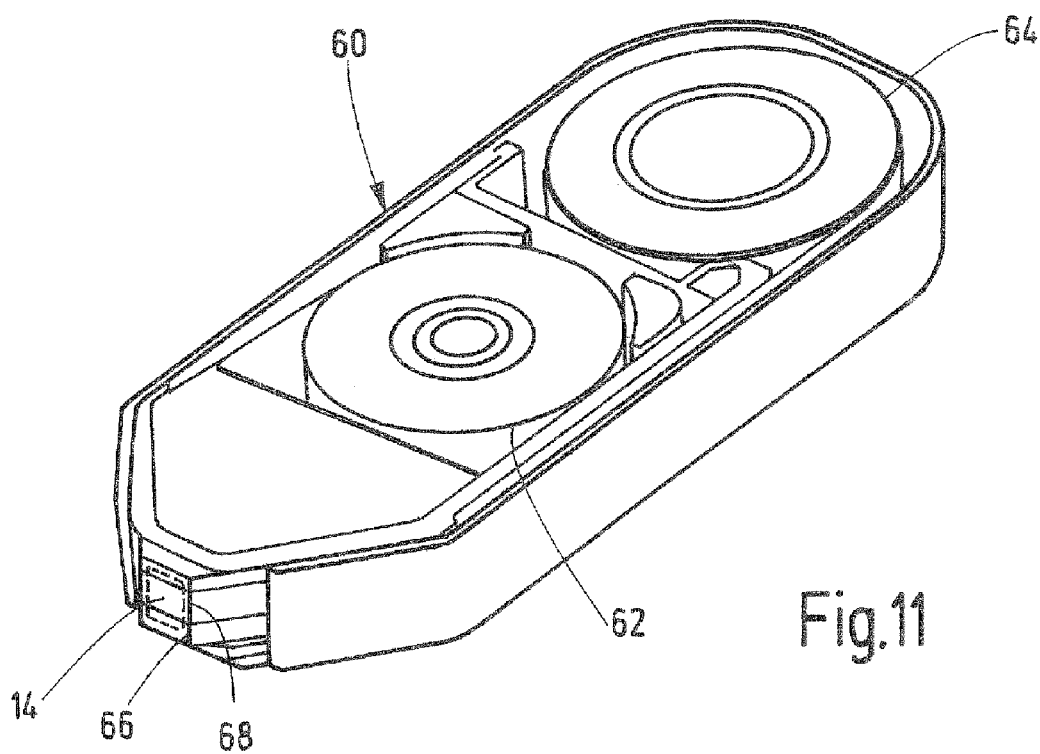
FIG. 11 shows a diagnostic tape cassette with a test tape stored therein in a broken perspective diagram.

The test tape 10 is inserted as a consumable into a hand-held device in the form of a tape cassette 60 shown in FIG. 11 in order to enable a patient to himself carry out a plurality of on-the-spot glucose tests (for example 50 tests). For this purpose the tape cassette 60 has an unwinding spool 62 to unwind unused test tape and a take-up spool 64 to wind on used test tape in the process of which the test tape 10 is pulled over an application tip 66 in order to successively provide the test fields 14 there for sample application. Further details of the measurement acquisition can be derived for example from EP-A 1 878 379 to which reference is explicitly made in this connection.

During tape transport the test tape is guided over the application tip 66 under a tape tension of about 4 N. In order to further reduce unwanted lifting effects of the spreading net 20 in this process, the radiuses of the deflection edges 68 must be suitably adjusted. The stress on the multi-component structure 12, 14 and thus the upward arching is greatly reduced by increasing the radiuses. However, radiuses which are too large increase the width of the tip 66 and thus result in a disadvantageous enlargement of the sample application area and of the required sample volume. In any case it should be ensured that it is tensioned in a planar manner between two deflection edges 68.

Although embodiments of the invention have been described using specific terms, such description is for illustrative purposes only, and it is to be understood that changes and variations obvious to the skilled artisan are to be considered within the scope of the claims that follow and their equivalents.

What is claimed is:

1. A tape cassette including a diagnostic test tape for liquid samples, in particular body fluids, comprising a flexible transport tape that is wound onto or can be wound onto a spool and a plurality of test fields applied to the transport tape that are distributed in the longitudinal direction of the tape, said test fields comprising a carrier strip applied to the transport tape, a detection layer located thereon and a spreading net spanning the detection layer for a two-dimensional uptake of liquid sample, wherein the spreading net is wider than the detection layer, wherein the spreading net is supported in the area of its side edges protruding over the detection layer by strips of adhesive tape as a lifting protection on the carrier strip and is secured against delamination from the detection layer, wherein the strips of adhesive tape and the detection layer have essentially the same thickness so that the spreading net is supported without steps.

2. The tape cassette according to claim 1, wherein the protection against lifting is arranged such that the distance between the spreading net and detection layer under the conditions of use is no more than 40 micrometers.

3. The tape cassette according to claim 1, wherein the protection against lifting is arranged such that the distance between the spreading net and detection layer under the conditions of use is less than 20 micrometers.

4. The tape cassette according to claim 1, wherein the spreading net is attached circumferentially to the carrier strip by an adhesive frame as a protection against lifting which runs all around the detection layer.

5. The tape cassette according to claim 1, wherein the carrier strip consists of a robust foil material the shear strength of which is more than 0.05 N/mm$^2$ and which has a peel strength of more than 1 N/mm.

6. The tape cassette according to claim 1, wherein the spreading net lies flat across the detection layer and the strips of adhesive tape.

7. A tape cassette including a diagnostic test tape for liquid samples, in particular body fluids, comprising a flexible transport tape that is wound onto or can be wound onto a spool and a plurality of test fields applied to the transport tape that are distributed in the longitudinal direction of the tape, said test fields comprising a detection layer and a spreading net spanning the detection layer for a two-dimensional uptake of liquid sample, wherein the spreading net is formed from a lattice-like fabric comprising fabric threads that cross at right angles, wherein the fabric is oriented obliquely to the transport tape such that all fabric threads run obliquely to the longitudinal direction of the tape.

8. The tape cassette according to claim 7, wherein the orientation of the fabric is defined such that under a tensile load the difference in the transverse contraction of the transport tape and of the fabric is minimized.

9. The tape cassette according to claim 7, wherein the fabric has an oblique orientation at a compensation angle $\alpha$ in a range between 5° and 40° where the compensation angle $\alpha$ is defined by the smallest angle between the longitudinal direction of the tape and the fabric threads.

10. The tape cassette according to claim 7, wherein the fabric has an oblique orientation at a compensation angle $\alpha$ in a range between 20° to 25° where the compensation angle $\alpha$ is defined by the smallest angle between the longitudinal direction of the tape and the fabric threads.

11. The tape cassette according to claim 7, wherein the transport tape consists of a foil material having a Poisson number of 0.3 to 0.5.

12. The tape cassette according to claim 7, wherein the transport tape consists of a foil material having a Poisson number of about 0.4.

13. The tape cassette according to claim 7, wherein the fabric in plain weave is formed from warp yarns and weft yarns, and that the warp yarns run nearer to the longitudinal direction of the tape than the well yarns.

14. The tape cassette according to claim 7, wherein the fabric threads consist of a monofilament thread material.

15. The tape cassette according to claim 14, wherein the monofilament thread material is a polyester.

16. The tape cassette according to claim 15, wherein the polyester is a PET.

17. The tape cassette according to claim 7, wherein the fabric threads are hydrophilically coated.

18. The tape cassette according to claim 7, wherein the spreading net is wider than the detection layer and includes protruding side edges glued to a carrier strip mounted on the transport tape, wherein the carrier strip carries the detection layer.

19. The tape cassette according to claim 7, wherein the test tape is guided over a deflection point of the tape cassette with a tape tension of more than 1 N for sample application.

20. The tape cassette according to claim 7, wherein:
said test fields include a carrier strip applied to the transport tape;
the spreading net is wider than the detection layer;
the spreading net is supported in the area of its side edges protruding over the detection layer by strips of adhesive tape on the carrier strip on opposite sides of the detection layer, the strips of adhesive tape providing a lifting protection of the spreading net and securing the spreading net against delamination from the detection layer; and
the strips of adhesive tape and the detection layer have essentially the same thickness so that the spreading net lies flat across the detection layer and the strips of adhesive tape.

* * * * *